(12) United States Patent
Rovegno

(10) Patent No.: US 6,817,976 B2
(45) Date of Patent: Nov. 16, 2004

(54) DEVIATED DISTAL VIEWING ENDOSCOPE

(75) Inventor: Jean Rovegno, La Ciotat (FR)

(73) Assignee: Tokendo (S.A.R.L.), La Ciotat (FR)

( * ) Notice: Subject to any disclaimer, the term of this patent is extended or adjusted under 35 U.S.C. 154(b) by 213 days.

(21) Appl. No.: 10/292,802

(22) Filed: Nov. 11, 2002

(65) Prior Publication Data

US 2003/0097044 A1 May 22, 2003

(30) Foreign Application Priority Data

Nov. 19, 2001 (FR) .......................................... 01 14936

(51) Int. Cl.[7] .............................................. A61B 1/06
(52) U.S. Cl. ........................ 600/173; 600/172; 600/137; 600/170
(58) Field of Search ............................... 600/160, 127, 600/129, 137, 170, 171, 172, 173, 175, 176

(56) References Cited

U.S. PATENT DOCUMENTS

| | | | | |
|---|---|---|---|---|
| 4,697,577 A | * | 10/1987 | Forkner ...................... | 600/173 |
| 4,858,001 A | * | 8/1989 | Milbank et al. .............. | 348/66 |
| 5,575,757 A | * | 11/1996 | Kennedy et al. ............. | 600/167 |
| 5,797,836 A | * | 8/1998 | Lucey et al. ................. | 600/109 |
| 6,626,828 B2 | * | 9/2003 | Dohi et al. .................. | 600/173 |
| 6,648,817 B2 | * | 11/2003 | Schara et al. ............... | 600/173 |
| 6,695,774 B2 | * | 2/2004 | Hale et al. ................... | 600/173 |

FOREIGN PATENT DOCUMENTS

| | | |
|---|---|---|
| EP | 0 260 856 A | 3/1988 |
| FR | 2 783 937 A | 3/2000 |
| GB | 2 322 944 A | 9/1998 |

* cited by examiner

*Primary Examiner*—Beverly M. Flanagan
(74) *Attorney, Agent, or Firm*—Harrison & Egbert

(57) ABSTRACT

A deviated distal viewing endoscope is disclosed, wherein the rotation of the probe rotation control ring controls the rotation of the endoscopic probe as well as the rotation of a rotating tube housed in the handle and in the distal end of which a deviator prism is housed; the rotation of a focusing control ring controls the translation of the ring that acts to house the ocular lens; and the rotation of the ring controls the translation of a first cylindrical mount housing an ocular lens; and the rotation of a viewing angle variation control ring controls the translation of a second cylindrical mount integral with a cylindrical maneuvering tube, a longitudinal displacement of which controlling the tilting of the deviator prism of the endoscope.

15 Claims, 4 Drawing Sheets

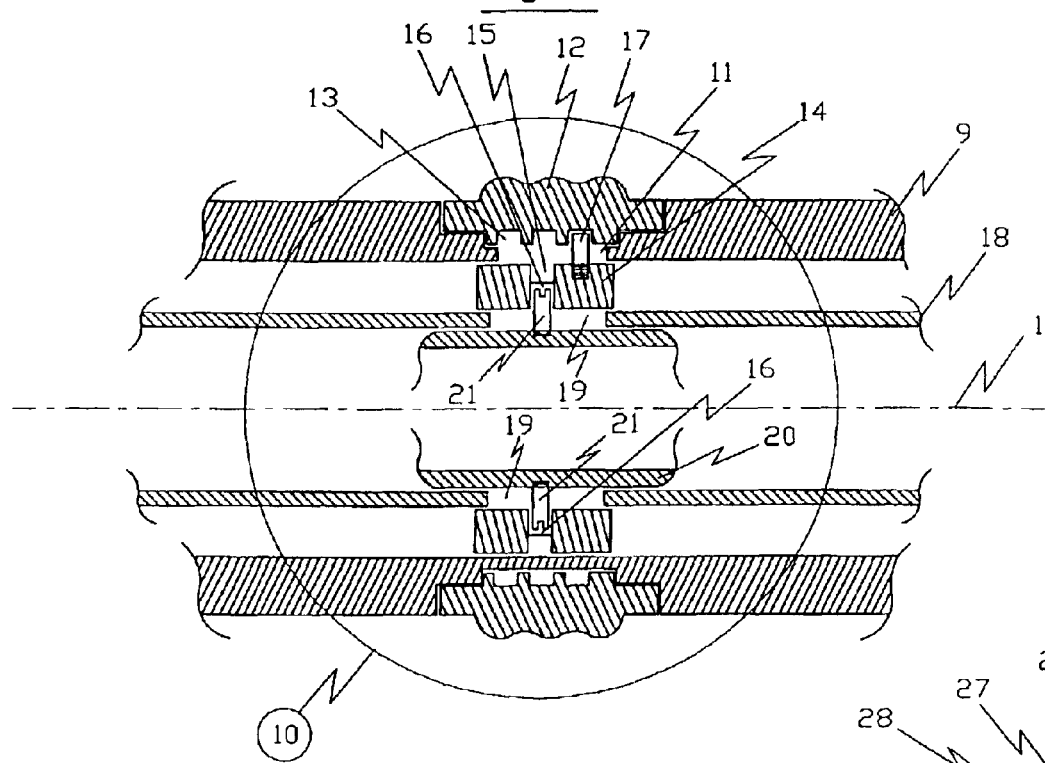
Fig I
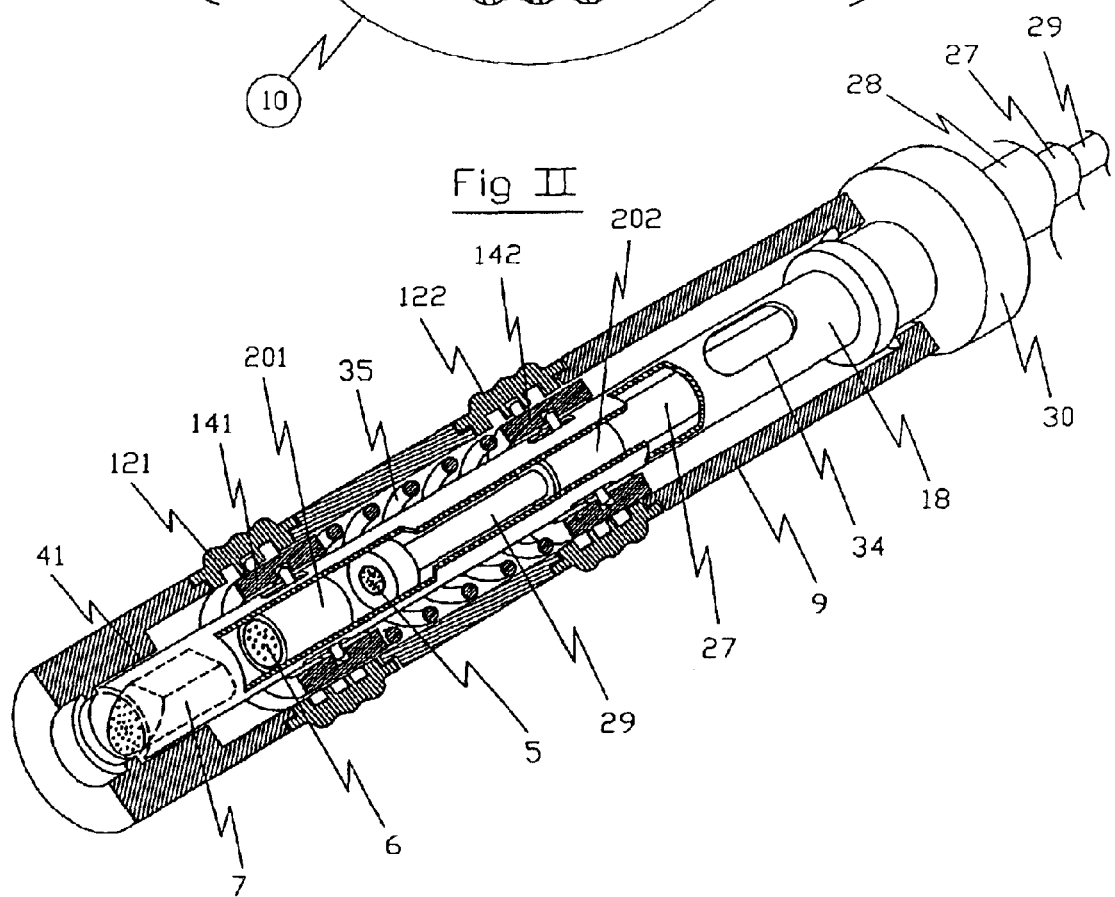
Fig II

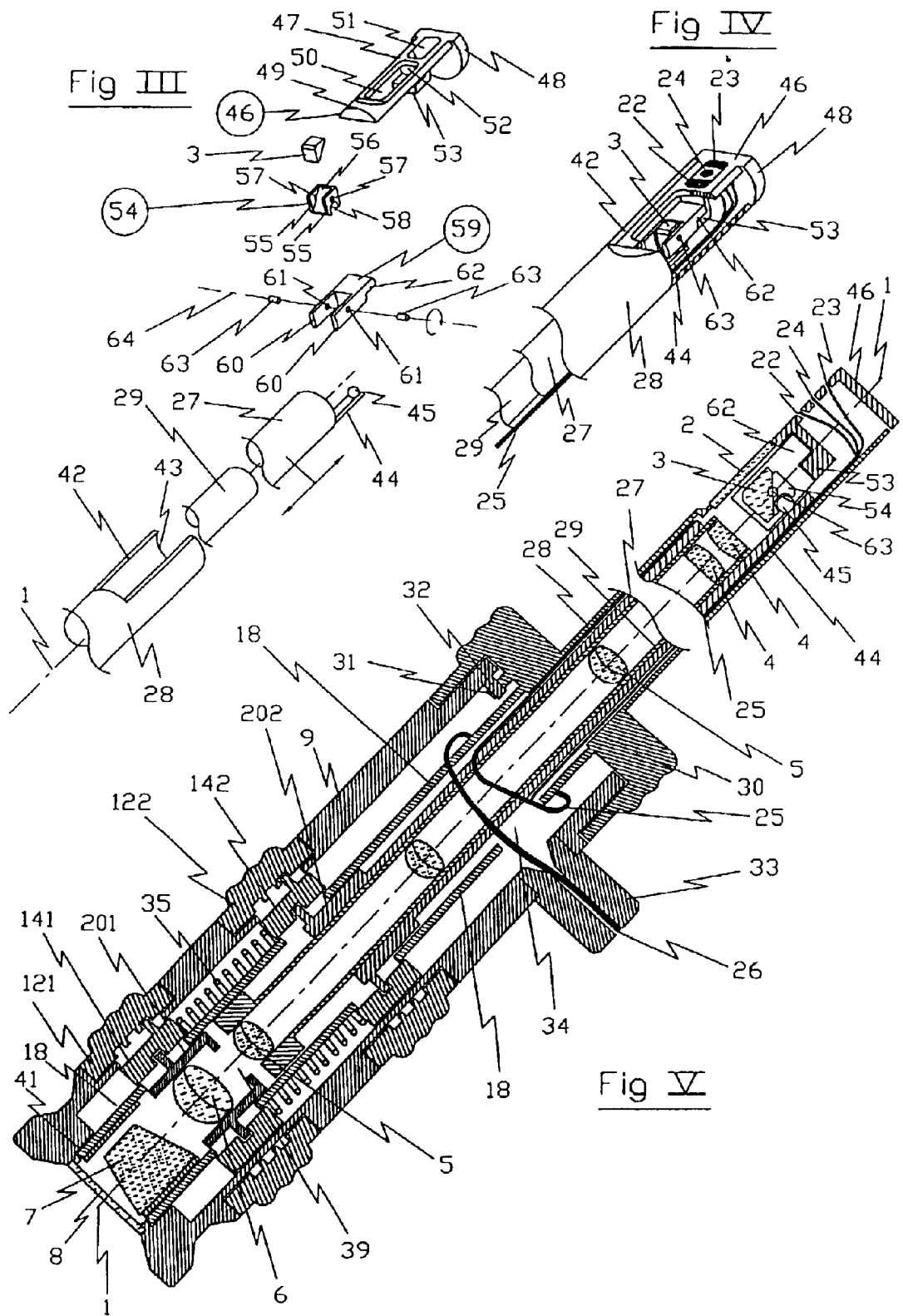

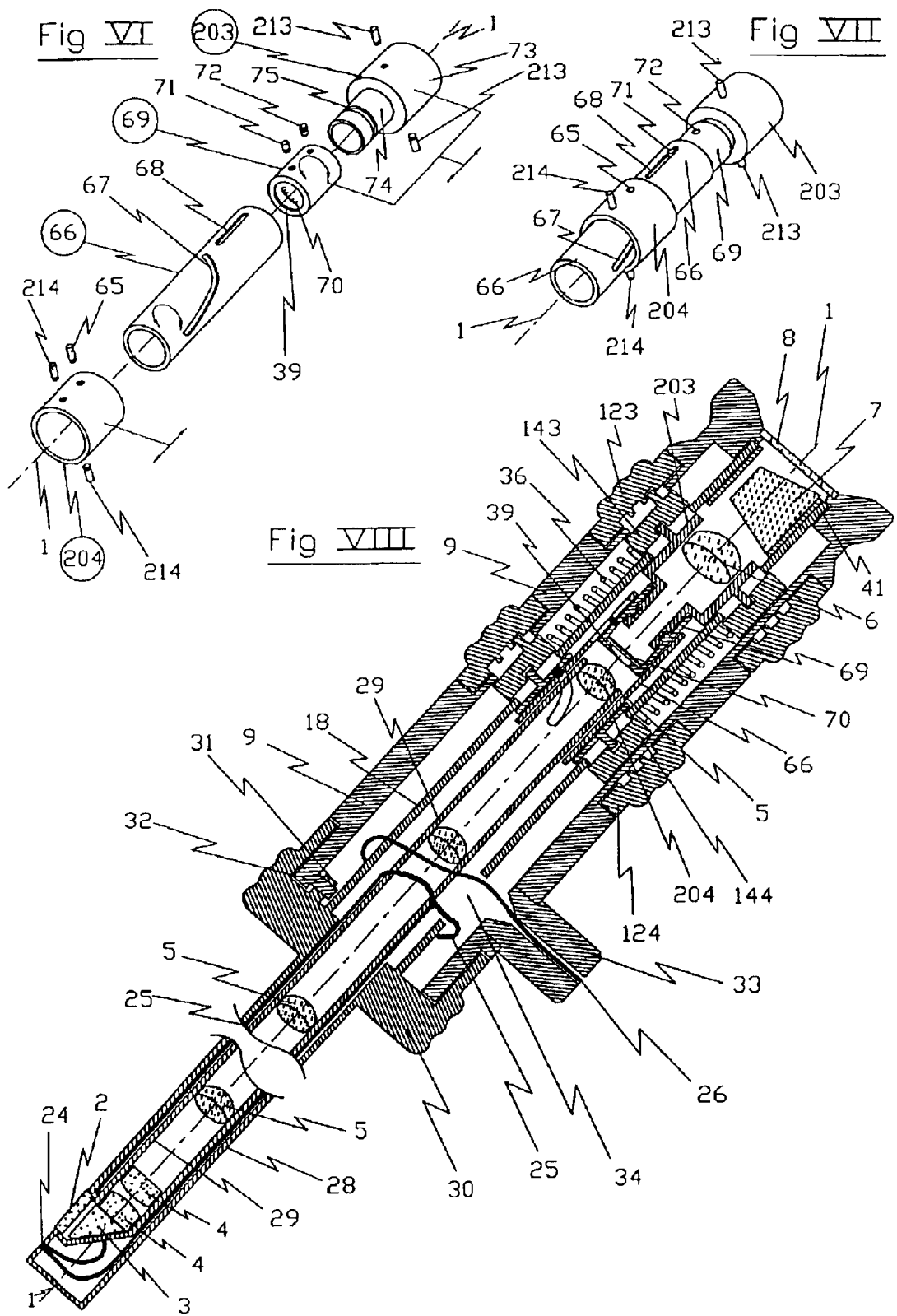

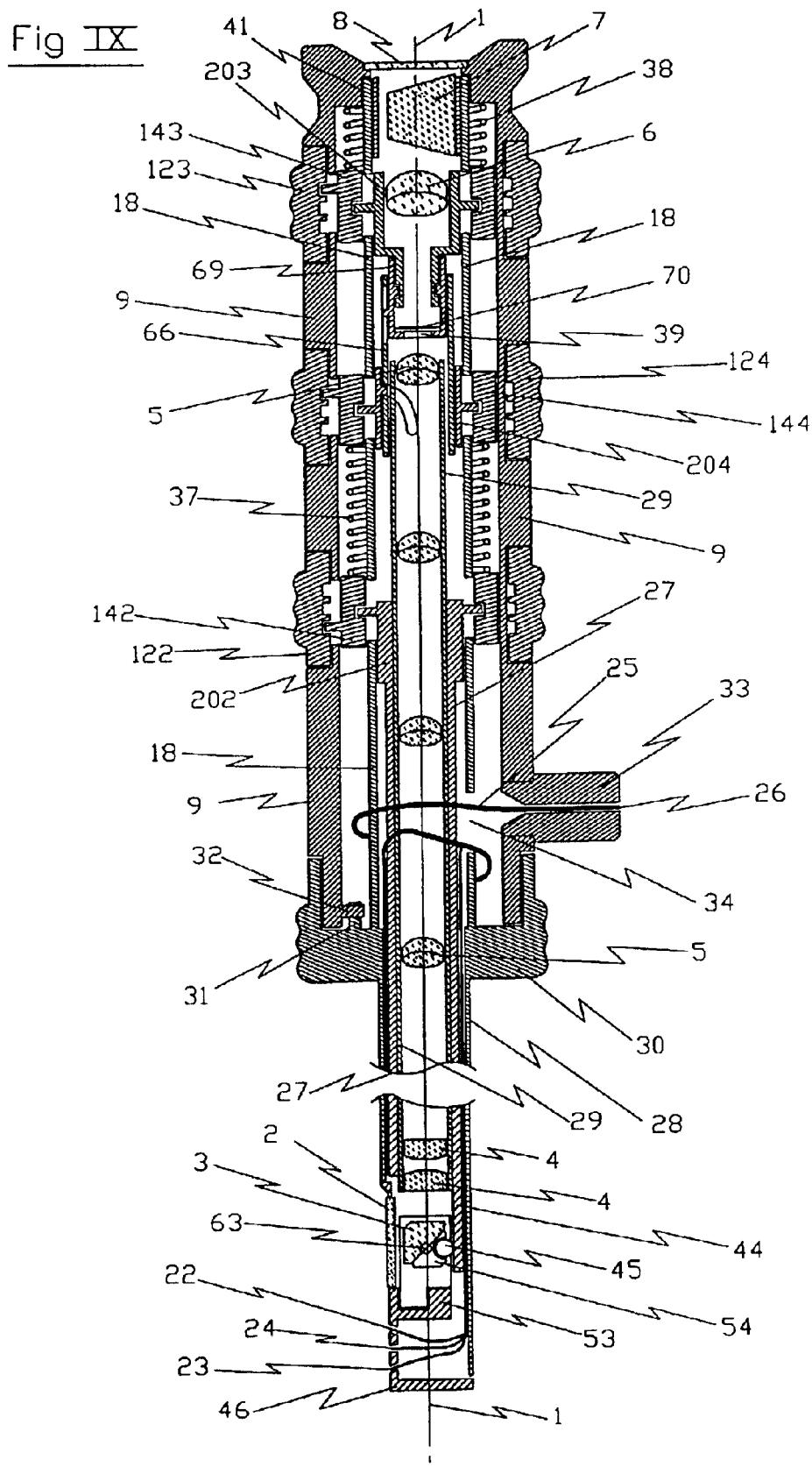

DEVIATED DISTAL VIEWING ENDOSCOPE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention involves a deviated viewing endoscope that has the advantage of all or part of the following options:

rotation of the viewing axis;

variation of the viewing angle;

rotation of the reticle; and focusing control.

BACKGROUND OF THE INVENTION

The term endoscope designates a rigid probe which, introduced into a lit cavity, makes it possible for the user to observe the inside of the cavity. In order to do this, an endoscope integrates by its nature, an optical device and a lighting device.

The term axial viewing endoscope designates an endoscope in which the optical axis of the distal lens is integrated with the mechanical axis of the endoscope. The optical device of an axial viewing endoscope comprises a frontal optical view port, a distal lens, a system for optical transport of an image generally comprised of a series of achromatic lenses and an ocular lens having a longitudinal displacement that makes it possible for the user to adjust the sharpness of the observed image. This optical device is calculated in a manner so that the image transmitted by the ocular lens does not have bi-directional inversion relative to reality. The lighting device of an axial viewing endoscope is comprised of a bundle of lighting fibers whose distal end generally comprises a lighting window in the form of a collar arranged around the frontal optical view port. The proximal end of the bundle of lighting fibers is housed in a lateral lighting seat integrated into the handle of the endoscope. The lighting field created by the distal lighting window covers the optical field of the endoscope when the lighting base is connected, by means of a lighting cable, to a light generator.

The term deviated viewing endoscope designates an endoscope in which the optical viewing axis forms an angle with the mechanical axis of the endoscope. The viewing is prograde if this angle is less than 90°, lateral if it is equal to 90°, and retrograde if it is greater than 90°. The optical device of a deviated viewing endoscope thus comprises in all cases a distal deviator prism.

If the distal prism is a deviator prism having total reflection characterized by a bi-directional inversion of the image transmitted by the prism, the optical device of the endoscope will comprise a lateral optical view port, the distal deviator prism, a lens, an optical system for transport of the image generally comprised of a series of achromatic lenses and an ocular lens whose longitudinal displacement makes it possible for the user to adjust the sharpness of the observed image. This optical system for transport of the image is calculated in a manner so that the image delivered by the ocular lens is not totally inverted relative to reality.

If the distal prism is a deviator prism having partial reflection characterized by a unidirectional inversion of the image transmitted by the prism, the optical device of the endoscope will comprise a lateral optical view port, the distal deviator prism, a lens, an optical system for the transport of an image generally comprised of a series of achromatic lenses, a correcting prism introducing a unidirectional inversion of the image transmitted by the prism and an ocular lens whose longitudinal displacement makes it possible for the user to adjust the sharpness of the observed image. The radial positioning of the correcting prism and the structure of the optical transport system is calculated in a manner so that the image delivered by the ocular lens is not partially inverted relative to reality. The deviated viewing endoscopes having adjustable focus equipped with a distal deviator prism having partial reflection have two main types of architecture. The first of these architectures involves endoscopes where the correcting prism is directly integrated into the optical system for transport of the image, the low dimensions of this correcting prism comprising a handicap in these conditions, as far as the luminosity is concerned. The second architecture mentioned appears for the first time in the patent dated 1938 (Louis K-PITMAN/U.S. Pat. No. 2,118,523/1938), and involves the endoscopes whose correcting prism comprises the proximal end of the optical device. In this case, it rapidly appeared as very advantageous to implement in the proximal part of the endoscope a cylindrical mount functioning to house the ocular lens, a mount whose proximal end shelters the correcting prism and whose distal end contains a field diaphragm (field stop) positioned in the distal focal plane of the ocular lens. The focusing control of the endoscope is done in longitudinally displacing this mount. This type of device, described since 1961 by the American company ACMI (U.S. Pat. No. 2,990,830/1961) has since been adopted by numerous endoscope manufacturers.

The lighting device of a deviated viewing endoscope is itself generally comprised of a bundle of lighting fibers whose distal end comprises a lateral lighting window located between the lateral optical view port and the distal end of the endoscope, the axis of lighting of this window being approximately parallel to the optical viewing axis of the endoscope. The proximal end of the bundle of fibers is housed in a lateral lighting seat integrated into the handle of the endoscope. The lighting field created by the lateral lighting window covers the optical field of the endoscope when the lighting seat is connected, by means of a lighting cable, to a light generator.

The problems of operation peculiar to customary deviated viewing endoscopes involve the panoramic exploration of the inside of a cavity. Such an examination actually requires the user to make the endoscope go through a rotation of 360° around its mechanical axis, an operation that is rendered difficult by the presence of the lighting cable united with the lighting seat of the endoscope. These operational problems are the origin of the development of deviated distal "rotary" viewing endoscopes designated according to the manufacturers under the terms of "rotascope" (HENKE SASS WOLF), of "endoscope having a turning shell" (EFER), of "boroscope having a rotating light connector" (KARL STORZ), of "technoscope having a rotary light connector" (RICHARD WOLF) or of "borescope having orbital scanning" (OLYMPUS). All of these endoscopes use a deviated distal endoscopic viewing probe whose proximal end turns to the inside from a handle equipped with a ring that controls the rotation of the probe, of a lateral seat for the connection of a lighting cable, a ring for adjusting the focus, and a proximal vision eye-piece cup. This type of architecture allows the user to make the endoscopic probe go through a rotation around its axis without changing the position of the lighting cable connected to the lateral lighting seat of the endoscope. The optical devices implemented in the different rotary endoscope models cited above can be classed in one of three families described in the following.

The first family of rotary endoscopes, developed numerous years ago notably by the German company HENKE-SASS WOLF, involves endoscopes having the optical device integrated in the rotating endoscopic probe and comprised of a distal deviator prism having total reflection, of a lens and of an optical system for transport of the image. The image delivered by the proximal end of the turning endoscope probe is transmitted to an ocular lens that is fixedly connected to a field diaphragm (field-stop) positioned in its distal focal plane and housed in a sliding manner in the handle of the endoscope, the longitudinal displacement of the ocular lens being controlled by an adjustment ring for focusing. The main disadvantage of the optical device described above results from the use of relatively expensive prisms having total reflection that are difficult to implement on a large scale of dimensions and deviation angles. The German company HENKE-SASS WOLF in 1989 described (German patent 0.371.233/1989) an original handle that makes it possible to improve the ergonomics of the controls of a rotary endoscope of this type.

The second family of rotary endoscopes, developed at the beginning of the 80's notably by the French company EFER, involves endoscopes having the optical device integrated in the rotating endoscopic probe and comprised of a distal deviator prism having partial reflection, of a lens and of an optical system for transport of the image inside of which a correcting prism is inserted. The image delivered by the proximal end of the turning endoscope probe is transmitted to an ocular lens that is fixedly connected to a field diaphragm (field-stop) positioned in its distal focal plane and housed in a sliding manner in the handle of the endoscope, the longitudinal displacement of this ocular lens being controlled by an adjustment ring for focusing. The main disadvantage of the solution described above results from the fact that the low dimensions of the correcting prism integrated in the optical system for transport of the image of the rotating endoscopic probe limit the overall luminosity of the endoscope and in practice prohibit the implementation of such an optical device in endoscopic probes having a low diameter. One model of the endoscope of this type marketed at the end of the 90's by the Japanese company OLYMPUS has nevertheless been described in a patent submitted in 1998 by the English company KEYMED (UK patent 2.322.944/1998).

The third family of rotary endoscopes involves endoscopes having the optical device integrated in the rotating endoscopic probe and comprised of a distal deviator prism having partial reflection, of a lens and of an optical system for transport of the image. The image delivered by the proximal end of the optical system for transport of the image integrated in the rotating endoscopic probe is transmitted to an ocular lens fixed in a mount housed in the handle of the endoscope, the ocular lens to which a correcting prism housed in the proximal end of the mount and a field diaphragm positioned in its distal focal plane are affixed. The proximal end of the rotating endoscopic probe is mechanically affixed to the mount in such a way that the distal deviator prism of the endoscopic probe and the correcting prism maintain the same relative alignment during a rotation of the probe around its axis. It is admittedly noted that the process consists in synchronizing the rotation of a deviator prism having partial reflection located at the distal end of an optical system with the rotation of a correcting prism located at the proximal end of the optical system has been described copiously in various patents involving the implementation of telescopes or periscopes (ERNST LEITZ GMBH/UK PATENT 1.272.742/1965, LUDWIG PIETZCH/GERMAN PATENT 28 33 944/1978, THEODOR PREUSSNER/UK PATENT 2.187.303/1987, THEODOR PREUSSNER/U.S. Pat. No. 4,787,725/1988). The synchronization of a distal deviator prism having partial reflection and a proximal correcting prism has also been implemented since 1977 in a distal deviated binocular rotary viewing endoscope described by JERRALD WIDRAN (U.S. Pat. No. 4,061,135/1977). In the case of a distal deviated rotary viewing endoscope, the device for correction of the direction of the image consists in coupling in rotation the endoscopic probe, and the mount that combines the field diaphragm, the ocular lens and the correcting prism must actually be connected to a focusing device that makes it possible to longitudinally move the mount relative to the proximal end of the endoscopic probe.

The process that falls within the public domain consists in connecting the proximal end of a rotating endoscopic sensor to a mount that combines a field diaphragm, an ocular lens, and a proximal correcting prism was implemented at the end of the 80's by the German company RICHARD WOLF. The architecture adopted by this manufacturer is characterized by the structure of the handle of these endoscopes which have two distinct mechanical parts coupled in rotation: a distal "fixed" part that uses a ring for controlling the rotation and a lateral seat for connecting the lighting cable, and a proximal "rotating" part that uses an adjustment focusing ring that controls the longitudinal displacement of the mount that combines the field diaphragm, an ocular lens, and a correcting prism, where the mount is housed in a sliding manner inside the proximal part. The proximal end of the endoscopic probe, which rotates freely inside the distal part of the handle, is mechanically united with the proximal part of the handle. The German company KARL STORZ described in 1990 (U.S. Pat. No. 5,088,819/1992) an original handle that makes it possible to improve the ergonomics of the controls of a rotary endoscope of this type. The main disadvantage of the solution described above results from the fact that the rotation of the endoscopic probe leads to the rotation of the proximal part of the handle and thus the rotation of the eye-piece cup of the endoscope located in front of the user's eye.

An original architecture that makes it possible to avoid this major disadvantage was implemented in 1992 by the French company EFER in the context of equipment for video thoracoscopy comprised of a rotary endoscopic probe having lateral sighting using a proximal focus control connected to a video camera. A similar architecture has been implemented in the deviated distal rotary viewing endoscopes marketed by the Japanese company OLYMPUS and described in the patents registered in 1993 by the English company KEYMED (UK PATENT GB 2 280 514, EUROPEAN PATENT EP 0 636 915, U.S. Pat. No. 5,540,650). A comparable architecture has also been described in a patent registered in 1998 by the French company TOKENDO (French patent FR 97 04569). All of the endoscopes relating to this type of architecture are characterized by specific mechanical coupling devices which the mount that combines the field diaphragm, the ocular lens and the correcting prism uses in advantageous way, whereby the mount is housed in a sliding manner and rotating inside the handle of these endoscopes. A first coupling device having a sliding nature makes it possible to transmit its rotational movement to the mount at the proximal end of the endoscopic probe, and regardless of the longitudinal position of the mount in the handle. A second coupling device makes it possible for the focus control ring to longitudinally displace the mount in the handle, regardless of the radial positioning of the mount in the handle. The solution described above, though notably improved in 2000 by the French company TOKENDO (French patent 98 12404) does not have any lower a number of serious disadvantages as a result of the mechanical tolerances that the complex kinematical devices connected to the mount that combines the field diaphragm, the ocular lens, and the correcting prism necessarily present, tolerances that lead to:

variations of the angular alignment between the distal deviator prism of the endoscopic probe and the correcting prism, variations manifested in random orientation defects of the image transmitted by the endoscope; and variations in centering the correcting prism on the optical axis of the endoscope, variations manifested in random angular deviations of the output axis of the image transmitted by the endoscope.

The deviated distal rotary viewing endoscope and proximal focusing described in 2000 by the TOKENDO company (French patent FR 98 11826/ German patent DE 19942 152 A1/ U.S. Pat. No. 6,346,076/ British patent 2.342.462) has the advantage of an original opto-mechanical structure that makes it possible to eradicate definitively the mechanical alignment and centering defects mentioned above. The correcting prism of this endoscope is in fact permanently affixed in the proximal end of a cylindrical tube housed in a rotating manner in the handle of the endoscope and has its distal end that is united so that it is affixed to the proximal end of the rigid rotating endoscopic probe connected to this handle. The ocular lens of this endoscope and the field diaphragm connected to it is affixed in a cylindrical mount housed in a manner so that it slides in the median part of the cylindrical tube. A mechanical coupling device connected to an external ring for controlling the focus makes it possible to displace the mount longitudinally inside the cylindrical tube. The coupling device prevents any interference between the rotational movement of the cylindrical tube and the longitudinal translation movement inside of the tube of the mount of the ocular lens.

The different types of rigid rotary distal viewing endoscopes described above thus make easier the panoramic exploration of the inside of a cavity while allowing the user to turn the viewing axis of these endoscopes through 360°. Another category of rigid endoscopes offers a response to the same ergonomic problem: this involves endoscopes, generally called "endoscopes having a dove prism" whose user can make the optical viewing angle vary. The opto-mechanical devices implemented in such a context can fall under two different concepts.

The first of these concepts, described in 1987 in detail by the American company BAXTER (U.S. Pat. No. 4,697,577) involves endoscopes in which the rotation of the viewing axis in a plane parallel to the axis of the endoscopic probe is implemented by a distal deflection device comprised of two deviator prisms having partial reflection. The first of these prisms, fixedly connected to the distal end of the lens of the endoscope, introduces an optical deviation of 90°. This fixed prism is connected to a second mobile prism that also introduces a deviation of 90° and is able to rotate around an axis perpendicular to the optical axis of the lens of the endoscope in a manner such that the optical input axis of the fixed prism and the optical axis of the mobile prism outlet are constant during the rotation of the mobile prism. Such an endoscope makes necessary a proximal correcting device that is comprised of two correcting prisms having partial reflection housed in the handle of the endoscope. The first of these prisms is a fixed prism designed to correct the unidirectional reflection introduced by the fixed prism of the distal deviation device. This fixed prism is connected to a second mobile prism rotating in synchronization with the mobile prism of the distal deviation device in a manner so as to permanently correct the unidirectional reflection introduced by the prism. A distal architecture similar to that mentioned above has been described in 1999 by the English company KEYMED (WO 0122865/2001). All of the endoscopes relating to the concept mentioned above have the advantage of a path of very sizeable variation of the viewing angle (on the order of 120°) making it possible to perform axial, prograde, lateral and retrograde observations. On the contrary, the intrinsic fragility of the distal optical view port specific to this type of endoscope makes their use in an industrial setting very marginal.

The second concept of an endoscope having a dove prism involves deviated viewing endoscopes in which the rotation of the viewing axis in a plane that contains the optical axis of the endoscopic probe implements a unique deviator prism having partial reflection housed in front of the distal end of the lens of the endoscope and able to turn around an axis perpendicular to the optical axis of the lens in a manner so that the optical axis of the output of the prism coincides with the optical axis of this lens. The optical device that makes it possible to correct the partial reflection introduced by the distal deviator prism can be in this case comprised of a simple prism correcting the partial reflection directly integrated into the optical system for the transport of the image from the endoscope according to a process described in 1965 by the French Atomic Energy Authority (UK PATENT 1.155.390/1966), process whose disadvantages as concerns luminosity have already been mentioned above. The proximal correcting and focusing device integrated into the handle of a bronchoscope designed in Russia and the object in 1963 of a patent registration in the USA (U.S. Pat. No. 3,096,756) comprises a more advantageous solution. This bronchoscope implements a cylindrical mount acting as housing for the ocular lens, the proximal end of which the correcting prism, and the distal end of which contains a field diaphragm fixedly positioned in the distal focal plane of the ocular lens. The focusing control of this bronchoscope is done by longitudinally displacing the mount. The path of the variation of the viewing angle of this type of endoscope, practically limited to approximately 70°, does not make possible axial observations. Their distal architecture makes it possible, on the contrary, to implement endoscopic probes having low diameters that are particularly robust.

It is rapidly appeared to be very interesting to improve the characteristics of a rigid deviated viewing endoscope by integrating simultaneously in the handle of the endoscope a proximal focusing device, a device for controlling the rotation of the viewing axis, and a device for controlling the tilting of the distal deviator prism. In 1998, the German company, KARL STORZ, described (WO 00/1199) a handle of a rigid deviated viewing endoscope integrating the three devices mentioned above. Although this document describes in a detailed manner the ergonomics of the handle, it does not provide, on the contrary, any information on the optical and mechanical mechanisms that make it possible to achieve this result. The only significant device described in this document involves the tilting of the distal deviation prism which is controlled by the longitudinal displacement of a metallic shaft arranged in parallel to the tube that functions for the housing of the optical system for transport of the image, the architecture having a cluttering that proves to be less favorable for the realization of endoscopes having low diameters.

A simple manner of estimating the dimensions of the surface defects of a mechanical part observed using an endoscope consists in positioning a reticle in the distal focal plane of the ocular lens of the endoscope. In these conditions, the image of this reticle is superposed on the observed endoscopic image by the user, and this even if a device for proximal focusing makes it possible to displace longitudinally a mount that integrates the ocular lens and the reticle. It thus appears of interest to offer to the user a simple method of "making the reticle turn in the image", this mechanism consisting simply in making the cylindrical mount turn around its axis in which the reticle and the ocular lens are housed. The document WO 99 56165 registered in 1998 by the English company KEYMED describes a deviated rigid viewing endoscope integrating simultaneously a device for rotation of the viewing axis, a device for proximal focusing, and a device for rotation of the reticle connected to the ocular lens of this endoscope. The area of application of the endoscope described in the document proves to be severely limited due to the integration of the correcting prism in the optical system for transport of the image, an arrangement for which the disadvantages as concerns the luminosity have been emphasized above several times.

The invention presented here has the purpose of describing a deviated distal viewing endoscope equipped with a partial distal reflecting prism and a proximal correcting prism having large dimensions, and able to integrate all or a part of the following devices:

rotational devices of the viewing axis;
devices for tilting the viewing axis;
device for proximal focusing; and
device for rotation of the reticle.

BRIEF SUMMARY OF THE INVENTION

The present invention involves deviated endoscopes having rotating probes and distal sighting whose structure results from the connection of the devices described below.

1. A mechanical assembly that combines a cylindrical tubular handle and a rotating probe, the probe comprising a cylindrical internal tube connected affixed to an external metallic tube whose proximal end is united with a control ring surrounding in a rotating manner the distal end of the handle. The ring is also united with the distal end of a cylindrical tube housed in the handle and the proximal extension of the internal tube of the probe. The proximal end of the tube housed in the handle is surrounded by a cylindrical bearing arranged inside of the proximal end of the handle.

2. A stopper device designed to limit the range of rotation of the endoscopic probe.

3. An optical device comprised of a lateral view port integrated in the distal part of the external tube of the probe, a deviator prism having partial reflection, a lens housed in the distal part of the internal tube of the probe, an optical system for transport of the image housed in the internal tube, an ocular lens arranged in the tube housed in the handle and united with the rotating probe, a correcting prism for partial reflection housed in the proximal end of the tube and radially positioned in a manner so as to offset the unidirectional inversion of the image introduced by the distal deviating prism, and a transparent window housed in the proximal opening of the handle.

4. A lighting device comprised of a bundle of optical fibers housed in the annular volume comprised between the external and internal tubes of the rotating probe. The distal end of this bundle opens into one or more lighting windows arranged in the distal part of the external tube of the probe in a manner so that the lighting field covers the optical field of this probe. The proximal part of this bundle of fibers opens to the inside of the handle through a hole made in the tube housed in the handle and united with the rotating probe. The proximal end of this bundle of fibers is housed in the end of a lateral seat united with the handle and designed to be connected to the lighting cable. The proximal part of the bundle of fibers is coiled around the tube housed in the handle and united with the turning probe, this in order to prevent the rotation of the probe from causing the stresses able to break the fibers of this bundle.

5. Several independent mechanical devices each having a control ring surrounding the handle, where the rotation of the ring causes the longitudinal displacement of a cylindrical mount inside the tube housed in the handle and united with the turning probe. The kinematical structure of these devices prevents any interaction between the rotational movement of the probe and the translational movements of the cylindrical mount and the rotation of its control ring.

The devices mentioned above make it possible to realize and to integrate in a deviated distal rotary viewing endoscope all or part of the functions described as an example in the following:

Focusing control: device making it possible to longitudinally displace a cylindrical mount acting as the housing of an ocular lens of the endoscope;

Control for the variation of the viewing: device making it possible to longitudinally displace a cylindrical mount comprising the proximal end of a maneuvering tube housed in a sliding manner around the internal tube of the probe. The longitudinal displacement of the distal end of the maneuvering tube controls the around an axis perpendicular to the probe of the distal deviating prism having partial reflection of the endoscope; and Control of the rotation of the reticle: device that makes it possible to displace longitudinally a cylindrical mount that uses a radial cylindrical finger housed in a manner running in a helicoidal groove arranged in the distal part of a cylindrical tube whose proximal end functions to be housed in a transparent reticle positioned in the distal focal plane of the ocular lens of the endoscope.

BRIEF DESCRIPTION OF THE SEVERAL VIEWS OF THE DRAWINGS

FIG. I shows a sectional view of the structure of the devices for controlling the implementation in the deviated distal rotary viewing endoscopes relating to the present invention.

FIG. II shows a sectional view of the structure of the handle of a rotary endoscope equipped with a distal deviator handle having a partial reflection, relating to the present invention and having the simultaneous advantage of a focusing control and control of the variation of the viewing angle.

FIG. III shows an exploded perspective view of the various specific mechanical components integrated in the distal end of a deviated distal viewing endoscope that has the advantage of a device for varying the viewing angle relative to the present invention.

FIG. IV shows an inner perspective view of the distal structure of a distal viewing endoscope having the advantage of a device for the variation of the viewing angle relating to the present invention.

FIG. V shows a sectional view of the structure of a rotary endoscope equipped with a distal deviator prism having partial reflection, relating to the present invention, and simultaneously having the advantage of a focusing control and a control for the variation of the viewing angle.

FIG. VI shows an exploded perspective view of the various mechanical components comprising a coupling device specifically integrated in the handle of a rotary distal viewing endoscope relating to the present invention and simultaneously having the advantage of a focusing control and a control for rotation of the reticle.

FIG. VII shows an upper perspective view of the coupling device specifically integrated in the handle of a deviated rotary distal viewing endoscope relating to the present invention and simultaneously having the advantage of a focusing control and a control for rotation of the reticle.

FIG. VIII shows a sectional view of the structure of a rotary endoscope equipped with a distal deviator prism having partial reflection, relating to the present invention, and simultaneously having the advantage of a focusing control and a control for rotation of the reticle.

FIG. IX shows a sectional view of the structure of a rotary endoscope equipped with a distal deviator prism having partial reflection, relating to the present invention, and simultaneously having the advantage of a focusing control, a control for rotation of the reticle, and a control for the variation of the viewing angle.

DETAILED DESCRIPTION OF THE INVENTION

FIG. I

FIG. I shows the functioning principles of a kinematical device 10 that makes possible the control of any one of the various functions (focusing, variation of the viewing angle, rotation of a reticle) able to be integrated into deviated distal rotary viewing endoscopes which are the object of the present invention. Such a device 10 is controlled by an outside ring 12 that surrounds the cylindrical handle 9 of the endoscope in a rotational manner, the rotation of the ring causing the longitudinal displacement of a cylindrical mount 20 housed in a sliding manner inside a cylindrical tube 18 united with the rotating endoscopic probe connected to the cylindrical handle 9 and housed in a rotating manner in the handle.

The rotation around its axis 1 of the deviated distal viewing endoscopic probe causes the rotation inside of the cylindrical handle 9 of the cylindrical tube 18 affixed united with the proximal end of the endoscopic probe.

A cylindrical mount 20, housed in a sliding manner in the tube 18, uses two radial external cylindrical fingers 21 that are diametrally opposed and run in two longitudinal grooves 19 arranged in diametrally opposed manner in the tube 18. The ends of the fingers 21 are housed in a manner running in an annular groove inside the profile that is preferably square 16 arranged in a ring 14 surrounding the tube 18. The ring uses two radial openings 15 that are diametrally opposed and open into the inside annular groove 16, the openings making it possible to screw the two cylindrical fingers 21 into the cylindrical mount 20 after the ring 14 has been positioned around the tube 18.

The ring 14 uses an external radial cylindrical finger 17 housed in a manner so that it slides in a longitudinal slot 11 arranged in the cylindrical handle 9 of the endoscope, the end of the cylindrical finger being housed in a manner so that it runs in an helicoid groove inside the preferably square profile 13 arranged in the control ring 12 that surrounds the cylindrical handle 9.

The device 10 realized in this way makes possible the longitudinal displacement of the mount 20 inside the tube 18, and regardless of the radial positioning of the tube. The device also makes it possible for the cylindrical tube 18, and thus the mount 20 that is connected to it, to rotate freely inside the handle 9, and regardless of the longitudinal positioning of the mount.

FIG. II

FIG. II shows the functioning principles of the devices 10 implemented in the handle 9 of a deviated viewing endoscope relating to the present invention and simultaneously having the advantage of the following options:

rotation of the viewing axis around the axis of the endoscope;

variation of the viewing angle of the endoscope; and focusing control.

The deviated distal viewing endoscopic probe united with the control handle 9 is mechanically comprised of an internal tube 29 in which the optical system for transporting the endoscopic image is housed, of a maneuvering tube 27 that slides longitudinally around the tube 29 and acts for the transmission to the control device the variation of the viewing angle, and of an external tube 28 united affixed to the internal tube 29.

The proximal end of the external tube 28 of the endoscopic probe is affixed united with a rotation control ring 30 connected in a turning manner to the distal end of the control handle 9. The rotation around its axis of the deviated distal viewing endoscopic probe housed in the external tube 28 leads to the rotation, inside of the cylindrical handle 9, of the cylindrical tube 18, whose distal end is united affixed to the rotation control ring 30 and the proximal end acts as a housing of an optical correcting prism 7. The distal part of the tube 18 uses an opening 34 that acts for the passage to the proximal part of a bundle of lighting fibers housed in the annular volume between the tubes 27 and 28 of the endoscopic probe.

A first control device similar to the device 10 described above in the text relating to FIG. I is integrated in the proximal part of the control handle 9. The rotation of the external control ring 121 of the device causes the longitudinal displacement of an intermediate ring 141, a displacement which itself causes the longitudinal displacement inside the tube 18 of a cylindrical mount 201 in which an ocular lens 6 is fixedly housed. The ocular lens stays positioned over its entire path between the achromatic lens 5 that comprises the proximal end of the optical system for transport of the image housed in the tube 29 and the correcting prism 7 that is affixed housed in the proximal end of the tube 18. The device makes it possible for the user in these conditions to control the of the transmitted image by the correcting prism 7.

A second control device that is also similar to the device 10 described above in the text relating to FIG. I is integrated in the central part of the control handle 9. The rotation of the outside control ring 122 of this device causes the longitudinal displacement of an intermediate ring 142, a displacement which itself causes the longitudinal displacement inside the tube 18 of a cylindrical mount 202 that fixedly surrounds the proximal end of the tube 27 that slides around and along the tube 29 in which the optical system for the optical transport of the image of the endoscope is housed. The longitudinal displacement of the distal end of the tube 27 itself controls the tilting of the deviator prism of the endoscope according to the modes which are explained in the following in the texts relating to FIGS. III, IV and V. The device allows in these conditions for the user to control the viewing angle of the deviated viewing endoscope in which it is integrated.

A helicoidal spring 35 that surrounds the tube 18 is slightly compressed between the proximal side of the ring 142 and the distal side of the ring 141, the spring being designed so as to make up for the functional play of the two control devices mentioned above.

FIG. III

FIG. III shows the various specific components integrated into the distal end of a deviated viewing endoscope relating to the present invention and having the advantage of a control device for the variation of the viewing angle.

The mechanical component 46 is a distal end cap designed to be connected to the distal end of the external tube 28 of the endoscopic probe. The end cap has a transverse distal side designed to come to be supported on the distal side 43 of the tube 28 and a flat longitudinal side 47 that ends by a proximal connecting end 49, where the longitudinal side is designed to be supported on the notch 42 arranged in the distal end of the tube 28. The flat longitudinal side 47 of the end cap 46 uses a distal opening 51 designed to receive the distal end of the bundle of lighting fibers of the endoscope and a proximal opening 50 designed to receive a glass view port acting for the protection at the distal end of the optical device of the endoscope. The end cap 46 uses an internal protuberance 53 that has the shape of a set square that has a longitudinal part designed to act as a support for the distal end of the clevis 59.

The mechanical component 54 is designed to act as a support for the deviator prism 3 that comprises the distal end of the optical device of the endoscope. This component uses two lateral lugs 55 between which the prism 3 is housed and one internal inclined side 56 designed to act as a support for the reflecting side of the prism. The lugs 55 each use a transverse opening 57 designed to act as a receptacle for the ends of the two cylindrical fingers 63 acting as the pivoting axis the lower side of the support prism 54 has, in addition, a semi-circular transverse groove 58 designed to act for the housing of the metallic sphere 45 that is affixed to the tab 44 that comprises the distal end of the control tube 27.

The mechanical component 59 is a clevis on the inside of which the support 54 of the distal deviator prism 3 can pivot. This clevis 59 uses a distal end 62 designed to be affixed to the longitudinal part of the set square 53 of the distal end cap 46, and the two proximal lugs 60 between which the support of the prism 54 can pivot. The lugs 60 each have a transverse opening 61 designed to act for housing by two cylindrical fingers 63 that mark the transverse pivot axis 64.

The deviated distal viewing endoscopic probe is mechanically comprised of an inside tube 29 in which the optical system for transport of the endoscope image is housed, an external tube 28 affixed to the inside tube 29, and a maneuvering tube 27 sliding longitudinally around and along the inside tube 29 and whose longitudinal displacement acts to control the tilting of the distal deviator prism 3. The external tube 28 has a notch 42 designed to act to support the distal end cap 46, and the control tube 27 has a distal tab 44 on which the metallic sphere 45 is affixed whose rotation in the groove 58 arranged in the support of the prism 54 functions to control the tilting of the prism.

FIG. IV

FIG. IV shows the structure of the distal end of a deviated viewing endoscope relating to the present invention and having the advantage of a device for controlling the viewing angle.

The distal end cap 46 is affixed to the distal end of the external tube 28, and the distal end 62 of the clevis acting to house the support of the deviator prism 3 is affixed to the longitudinal branch 53 of the internal square that is used by the distal end cap 46. The longitudinal displacement of the distal end of the maneuvering tube 27 causes the tilting of the deviator prism around a transverse axis 63.

The distal portion of the bundle of lighting fibers 25 housed in the annular space between the external tube 28 and the maneuvering tube 27 is divided into three sub-bundles whose distal ends are introduced then glued into three lighting windows 22/23/24 arranged in the lateral distal opening of the end cap 46. The prism 3 is itself protected by an optical view port glued into the lateral proximal opening of the end cap 46.

FIG. V

FIG. V shows the structure of a deviated viewing endoscope relating to the present invention and simultaneously having the advantage of the following devices:
  rotation of the viewing axis around the axis 1 of the endoscope;
  variation of the viewing angle of the endoscope; and
  focusing control.

The mechanical structure of the endoscopic probe is organized around an external metallic tube 28 whose distal end is affixed to a distal end cap 46, an internal tube 29 affixed to the external tube 28, and a maneuvering tube 27 that surrounds the internal tube 29 in a sliding manner. The proximal end of the external tube 28 of the endoscopic probe is affixed to a rotational control ring 30 that surrounds the distal end of the cylindrical handle 9 of the endoscope so that it rotates. A stopper device limiting the range of rotation of the endoscopic probe is comprised of a longitudinal finger 31 united with the proximal side of the ring 30 and arranged in a manner so as to come into contact with an inside radial finger 32 united with the handle 9. The proximal side of the control ring for rotation 30 is affixed to the distal end of a cylindrical tube 18 housed in a rotational manner in the cylindrical handle 9 of the endoscope and having a proximal end that rotates freely in a bearing 41 arranged for this purpose inside the proximal end of the handle.

The optical device of the endoscope is comprised of a lateral view port 2 integrated in the distal end cap 46, a deviator prism for partial reflection 3 also integrated in the distal end cap 46, an objective comprised of several lenses 4 arranged in the distal end of the internal tube 29, an optical system for the transport of the image comprised of a series of achromatic lenses 5 arranged in the inside tube 29, an ocular lens 6 housed in a sliding manner in the cylindrical tube 18, a correcting prism 7 affixed in the proximal end of the cylindrical tube 18 and radially positioned in a manner so as to compensate for the unidirectional inversion of the image introduced by the distal deviator prism 3, and a protection glass 8 affixed so that it is housed in the proximal end of the cylindrical handle 9.

The lighting device integrated in the endoscope comprises a bundle 25 of optical lighting fibers housed in the annular volume between the sliding tube 27 and the external tube 28. The distal end of the bundle of fibers 25 is divided into three sub-bundles whose distal ends are glued then polished into three lateral lighting windows 22/23/24 arranged in the distal end cap 46. The directions of these windows are calculated in such a manner that the window 24 corresponds to a lateral lighting, the window 22 to a retrograde lighting, and the window 23 to a prograde lighting. The proximal part of the bundle of fibers 25 opens into the annular volume between the tube 18 and the distal part of the cylindrical handle 9 through a window 34 arranged in the distal part of the cylindrical tube 118. The proximal end of the bundle of fibers 25 is glued and then polished in the lateral seat 33 affixed to the distal part of the handle 9. Several turns of the bundle of fibers 25 are wrapped around the cylindrical tube 18 in the annular volume between the tube and the cylindrical handle in order to prevent a rotation of 360° of the endoscopic probe from leading to dangerous mechanical stresses on the bundle of fibers.

A first control device similar to the device 10 described above in the text relating to FIG. I is integrated in the proximal part of the control handle 9. The rotation of the external control ring 121 of the device causes the longitudinal displacement of the ring 141 surrounding the tube 18, a displacement which itself leads to the longitudinal displacement inside the cylindrical tube 18 of the cylindrical mount 201 in which the ocular lens 6 is fixedly housed, the distal opening 39 of which, positioned in the distal focal plane of the ocular lens, acts as the field diaphragm.

A second control device also similar to the device 10 described above in the text relating to FIG. I is integrated in the central part of the control handle 9. The rotation of the external control ring 122 of the device causes the longitudinal displacement of the ring 142, a displacement which itself leads to the longitudinal displacement inside the tube 18 of the cylindrical mount 202 that surrounds in an affixed manner the proximal end of the control tube 27 sliding around the internal tube 29. The longitudinal displacement of the spherical ball 45 that is affixed to the longitudinal tab 44 that comprises the distal end of the tube 27 leads to tilting around the transverse axis 63 of the mechanical support 54 of the deviator prism 3. The support 54 is housed in a clevis whose distal end 62 is affixed to the longitudinal branch 53 of the support in the shape of a set square arranged inside the distal end cap 46.

FIG. VI

FIG. VI shows the various specific components integrated in the handle 9 of a deviated viewing endoscope relating to the present invention and simultaneously having the advantage of the following devices:

rotation of the viewing axis around the axis 1 of the endoscope;

rotation of a reticle; and focusing control.

The mechanical component 203 is a part designed to be housed in a sliding manner in the proximal part of the tube 18 united with the endoscopic probe and housed in a rotating manner in the control handle 9 of the probe. The tubular component 203 uses a proximal cylindrical part 73 that acts as a mount for the ocular lens of the endoscope and a distal cylindrical part 74 of a lower diameter having an external annular groove 75.

The mechanical component 69 is a cylindrical tube whose proximal part is designed to surround the distal cylindrical part 74 of the component 203 and whose distal opening 39, which acts as the field diaphragm, functions to house a transparent support 70 on which the reticle of the endoscope is engraved. A transverse threaded finger 72 that can be screwed into the proximal part of the component 69, and whose internal end is designed to come to be housed in the annular external groove 75 machined around the distal end 74 of the component 203, makes it possible to connect the components 69 and 203 in a turning manner. The connection of these parts is done in a manner such that the reticle 70 housed in the distal opening 39 of the component 69 is positioned in the distal focal plane of the ocular lens housed in a fixed manner in the proximal part 73 of the mechanical component 203.

The mechanical component 66 is a cylindrical tube whose proximal part that uses a longitudinal slot 68 is designed to surround the distal part of the mechanical component 69, and whose distal part that uses a helicoidal slot 67 is designed to surround the internal tube that acts to house the optical system for transport of the image of the endoscope. A radial finger 71 that encircles the longitudinal slot 68 and can be screwed into the distal part of the mechanical component makes it possible to connect the components 66 and 69 in a sliding manner.

The mechanical component 204 is a cylindrical ring designed to be housed in a sliding manner in the central part of the tube 18 united with the endoscopic probe and housed in a turning manner in the control handle 9 of the probe. The ring 204 is dimensioned in order to surround the distal part of the mechanical component 66. A radial threaded finger 65 screwed into the proximal part of the ring 204 in a manner such that the end of the finger can circulate in the helicoidal slot 67 arranged in the distal part of the tube 66, makes it possible to connect the components 66 and 204 in a turning and sliding manner.

The proximal part 73 of the cylindrical component 203 uses two radial external fingers 213 designed to cause the longitudinal displacement of the component in the tube 18 united with the endoscopic probe, and due to a device identical to the one described in the text relating to FIG. I.

The distal part of the cylindrical component 204 uses the two external radial fingers 214 designed to cause the longitudinal displacement of the component in the tube 18 united with the endoscopic probe, and this due to a device identical to the one described in the text relating to FIG. I.

FIG. VII

FIG. VII shows the structure of the control devices integrated in the handle 9 of a deviated viewing endoscope relating to the present invention and simultaneously having the advantage of the following devices:

rotation of the viewing axis around the endoscope axis 1;

rotation of a reticle; and focusing control.

A control device identical to the one described in the text relating to FIG. I acts on the two diametrally opposed radial fingers 213 which are used by the cylindrical mount 203 in which the ocular lens 203 of the endoscope is affixed housed, and this in a manner so as to cause the longitudinal displacement of the mount.

The mounting finger 72, screwed into the proximal end of the cylindrical mount 69 whose distal opening, acting as the field diaphragm, also acts to house a transparent support on which the reticle of the endoscope is engraved, makes it possible to connect in a turning manner the mount 69, which surrounds the distal end of the mount 203, to the mount 203.

The mounting finger 71, screwed into the distal end of the cylindrical mount 69 and running in the longitudinal slot 68 arranged in the proximal part of the cylindrical tube 66, makes it possible to connect in a sliding manner the tube 66, which surrounds the distal end of the mount 69, to the mount 69.

The mounting finger 65, screwed into the proximal end of the cylindrical ring 204 and running in the helicoidal slot 67 arranged in the distal part of the tube 66, makes it possible to connect in a turning and sliding manner the ring 204 that surrounds the distal part of the tube 66 and the mount 66. A control device identical to the one described in the text relating to FIG. I acts on these two diametrically opposed radial fingers 214 used by the ring 204, and this in a manner so as to cause the longitudinal displacement of the ring.

FIG. VIII

FIG. VIII shows the structure of a deviated viewing endoscope relating to the present invention and simultaneously having the advantage of the following devices:

rotation of the viewing axis around the endoscope axis 1;

rotation of a reticle 70 positioned in the distal focal plane of the ocular lens 6; and focusing control.

The mechanical structure of the endoscopic probe is organized around an external metallic tube 28 that is affixed to an internal tube 29. The proximal end of the external tube 28 of the endoscopic probe is affixed to a rotation control ring 30 that surrounds in a rotating manner the distal end of the cylindrical handle 9 of the endoscope. A stopper device limiting the range of rotation of the endoscopic probe is comprised of a longitudinal finger 31 united with the proximal side of the ring 30 and arranged in a manner so as to stop on a radial internal finger 32 united with the handle 9. The proximal side of the rotation control ring 30 is affixed to the distal end of a cylindrical tube 18 housed in a turning manner in the cylindrical handle 9 of the endoscope and having a proximal end that rotates freely in a bearing 41 arranged for this purpose inside the proximal end of the handle.

The optical device of the endoscope is comprised of a lateral view port 2 integrated into the distal end of the external tube 28 of the endoscopic probe, of a deviator prism for partial reflection 3, of an objective comprised of several lenses 4 housed in the distal end of the internal tube 29 of the endoscope, of an optical system for transport of the image comprised of a series of achromatic lenses 5 arranged in the internal tube 29 of the endoscope, of an ocular lens 6 housed in the sliding mount 203, of a correcting prism 7 housed affixed in the proximal end of the cylindrical tube 18 and radially positioned in a manner so as to offset the unidirectional inversion of the image introduced by the distal deviator prism 3, and of a protection glass 8 housed affixed in the proximal end of the cylindrical handle 9.

The lighting device integrated in the endoscope comprises a bundle 25 of optical lighting fibers housed in the annular volume between the external tube 28 and the internal tube 29 of the endoscopic probe. The distal end of the bundle of fibers 25 is glued then polished in the lateral lighting window 24 arranged in the distal end of the external tube 28 of the endoscopic probe. The proximal part of the bundle of fibers 25 opens in the annular volume between the tube 18 and the distal part of the cylindrical handle 9 through a window 34 arranged in the distal part of the cylindrical tube 18. The proximal end of the bundle of fibers 25 is glued and then polished in the lateral seat 33 that is affixed to the distal part of the handle 9. Several turns of the bundle of lighting fibers 25 are wound around the tube 18 in the annular volume between the tube and the cylindrical handle in order to prevent a rotation of 360° of the endoscopic probe from causing dangerous mechanical stresses on the bundle of fibers.

A first control device similar to the device 10 previously described in the text relating to FIG. I is integrated into the proximal part of the control handle 9. The rotation of the external control ring 123 of the device causes the longitudinal displacement of the ring 143 surrounding the tube 18, a displacement which itself causes the longitudinal displacement inside the cylindrical tube 18 of the cylindrical mount 203 in which the ocular lens 6 is housed. The mount 203, which is connected in a turning manner to a cylindrical mount 69 that has an external diameter similar to that of the tube 29 of the endoscopic probe and has a distal opening 39 that acts as the field diaphragm, serves to house a transparent support 70 on which the reticle of the endoscope is engraved. The mount 69 comes to cover the distal end of the mount 203 in a manner so that the reticle 70 stays permanently positioned in the distal focal plane of the ocular lens 6.

A second control device similar to the device 10 previously described in the text relating to FIG. I is integrated into the median part of the control handle 9. The rotation of the external control ring 124 of this device causes the longitudinal displacement of the ring 144 surrounding the tube 18, a displacement which itself causes the longitudinal displacement inside the cylindrical tube 18 of a cylindrical ring 204.

A cylindrical tube 66 connects the cylindrical ring 204 and the mount that carries the reticle 69 according to the specifications described above in the texts relating to FIGS. VI and VII. The tube 66 surrounds the mount that carries the reticle 69 and the proximal end of the internal tube 29 of the endoscopic probe. The tube 66 is itself surrounded by the cylindrical ring 204. The distal end of the tube 66 uses a helicoidal slot in which a finger runs that is united with the ring 204, while its proximal end uses a longitudinal slot in which a finger runs that is united with the mount that carries the reticle 69.

The devices for control of the rotation of the reticle and focusing control are connected to a device for adjustment of the longitudinal play comprised of a helicoidal spring 36 that surrounds the median part of the cylindrical tube 18. The spring is compressed between the proximal side of the ring 144 of the device for control of the rotation of the reticle and the distal side of the ring 143 of the device for focusing control.

The kinematical architecture described above in the text relating to FIG. VII explains, in addition, the following devices:

the cylindrical mount 203 of the ocular lens 6 is connected in a turning manner to the cylindrical mount 69 of the reticle;

the mount 69 of the reticle is connected in a sliding manner to the proximal end of a cylindrical tube 66 whose distal end is itself connected in a turning and sliding manner to the cylindrical ring 204 by means of a finger that is united with the ring and runs in a helicoidal slot arranged in the distal part of this tube; and the ring 204 surrounds the tube 66 which itself surrounds the proximal end of the internal tube 29 of the endoscopic probe.

The kinematical architecture prevents any interaction between the rotation of the probe controlled by the external ring 32, the rotation of the reticle controlled by the external ring 124, and the longitudinal displacement of the ocular 6 controlled by the external ring 123.

FIG. IX

FIG. IX shows the structure of a deviated viewing endoscope relating to the present invention and simultaneously having the advantage of the following devices:

rotation of the viewing axis around the endoscope axis 1;

variation of the viewing angle of the endoscope;

rotation of a reticle 70 positioned in the distal focal plane of the ocular lens 6; and focusing control.

The mechanical structure of the endoscopic probe is organized around an external metallic tube 28 whose distal end is united with a distal end cap 46, of an internal tube 29 that is affixed to the external tube 28, and a median tube 27 that surrounds in a sliding manner the internal tube 29. The proximal end of the external tube 28 of the endoscopic probe is affixed to a ring for controlling the rotation 30 which surrounds the distal end of the cylindrical handle 9 of the endoscope a stopper device that limits the range of rotation of the endoscopic probe is comprised of a longitudinal finger 31 united with the proximal side of the ring 30 and arranged in a manner so as to come into contact with an internal radial finger 32 united with the handle 9. The proximal side of the rotation control ring 30 is united with the distal end of a cylindrical tube 18 that is housed in the cylindrical handle 9 of the endoscope and has its proximal end freely turning in a bearing 41 arranged for this purpose inside the proximal end of the handle.

The optical device of the endoscope is comprised of a lateral view port 2 integrated in the distal end cap 46, of a deviator prism for partial reflection 3 also integrated in the distal end cap 46, of an objective comprised of several lenses 4 housed in the distal end of the internal tube 29, of an optical system for transport of the image comprised of a series of achromatic lenses 5 arranged in the inside tube 29, of an ocular lens 6 housed in a sliding manner in the cylindrical tube 18, of a correcting prism 7 housed affixed in the proximal end of the cylindrical tube 18 and radially positioned in a manner so as to offset the unidirectional inversion of the image introduced by the distal deviator prism 3, and of a protection glass 8 housed affixed in the proximal end of the cylindrical handle 9.

The lighting device integrated in the endoscope consists of a bundle 25 of optical lighting fibers housed in the annular volume between the sliding tube 27 and the external tube 28. The distal end of the bundle of fibers 25 is divided into three sub-bundles whose distal ends are glued and then polished in three lateral lighting windows 22/23/24 arranged in the distal end cap 46. The directions of these windows are calculated in such a manner that the window 24 corresponds to a lateral lighting, the window 22 to a retrograde lighting, and the window 23 to a prograde lighting the proximal part of the bundle of fibers 25 opens into the annular volume between the tube 18 and the distal part of the cylindrical handle 9 through a window 34 arranged in the distal part of the cylindrical tube 18. The proximal end of the bundle of fibers 25 is glued and then polished in the lateral seat 33 affixed to the distal part of the handle 9. Several turns of the bundle of fibers 25 are wrapped around the cylindrical tube 18 in the annular volume between the tube and the cylindrical handle in order to prevent a rotation of 360° of the endoscopic probe from leading to dangerous mechanical stresses on the bundle of fibers.

A first control device similar to the device 10 described above in the text relating to FIG. I is integrated in the proximal part of the control handle 9. The rotation of the external control ring 123 of the device causes the longitudinal displacement of the ring 143 surrounding the tube 18, a displacement which itself leads to the longitudinal displacement inside the cylindrical tube 18 of the cylindrical mount 203 in which the ocular lens 6 is fixedly housed. The mount 203 is connected in a rotating manner to a cylindrical mount 69 that has an outside diameter similar to that of the tube 29 of the endoscopic probe and the distal opening 39 of which, acting as the field diaphragm, functions for the housing of a transparent support 70 on which the reticle of the endoscope is engraved. The mount 69 comes to cover the distal end of the mount 203 in a manner such that the reticle 70 stays permanently positioned in the distal focal plane of the ocular lens 6.

A second control device similar to the device 10 described above in the text relating to FIG. I is integrated in the central part of the control handle 9. The rotation of the external control ring 124 of the device causes the longitudinal displacement of the ring 144 surrounding the tube 18, a displacement which itself leads to the longitudinal displacement inside the cylindrical tube 18 of a cylindrical ring 204.

A cylindrical tube 66 connects the cylindrical ring 204 and the mount that carries the reticle 69 according to the specifications described above in the texts relating to FIGS. VI and VII. The tube 66 surrounds the mount that carries the reticle 69 and the proximal end of the internal tube 29 of the endoscopic probe. The tube 66 is itself surrounded by the cylindrical ring 204. The distal end of the tube 66 uses a helicoidal slot in which a finger runs that is united with the ring 204, while its proximal end uses a longitudinal slot in which a finger runs that is united with the mount that carries the reticle 69.

A third control device similar to the device 10 described above in the text relating to FIG. I is integrated in the central part of the control handle 9. The rotation of the external control ring 122 of this device causes the longitudinal displacement of the ring 142, a displacement which itself causes the longitudinal displacement inside the tube 18 of a cylindrical mount 202 that fixedly surrounds the proximal end of the tube 27 that slides around and along the tube 29. The longitudinal displacement of the spherical ball 45 affixed to the longitudinal lug 44 that comprises the distal end of the tube 27 causes the tilting of the deviator prism 3 around the transverse axis 63 of the mechanical support 54. The support 54 is housed in a clevis 59 whose distal end 62 is united with the longitudinal branch 53 of the support in the shape of a set square arranged inside the distal end cap 46.

The device for adjusting the focus of the endoscope is connected to a device for adjustment of the longitudinal play comprised of a helicoidal spring 38 that surrounds the proximal end of the cylindrical tube 18. The distal end of this spring comes to be supported on the proximal side of the loose ring 143 that surrounds the tube 18 while its proximal end comes to be supported on the distal side of the bearing arranged in the proximal end of the handle 9.

The devices for control of the rotation of the reticle and control of the variation of the viewing angle are connected to a device for adjustment of the longitudinal play comprised of a helicoidal spring 37 that surrounds the median part of the cylindrical tube 18. This spring is compressed between the proximal side of the ring 142 of the device for control of the variation of the viewing angle of the endoscope and the distal side of the ring 144 of the device for control of the rotation of the reticle.

Scope of the Invention

It goes without saying that the applications of the deviated rotary distal viewing endoscopes that are the object of the present invention can be both medical and industrial.

It also goes without saying that the present invention is in no way restricted to the embodiment modes and implementation modes that are described here in detail. On the contrary, the present invention covers all of the variations which can be conceived by the technical professional on the subject without necessarily diverging from the frame of the present invention, and notably endoscopes whose devices for capturing and/or transport of the image call for technologies different than those mentioned in the frame of the present invention.

I claim:

1. A deviated distal rotary viewing endoscope comprising:

a cylindrical tubular handle;

an endoscopic probe comprising an inside cylindrical tube and an external cylindrical tube affixed to said inside cylindrical tube and having a proximal end affixed to a probe rotation control ring controlling rotation of said endoscopic probe and surrounding a distal end of said handle in a turning manner, said probe rotation control ring being affixed to a cylindrical rotating tube housed in a turning manner in the handle, said inside tube having a proximal extension opening into the rotating tube; and an optical device comprising a lateral view port integrated in a distal part of said external tube, a deviator prism, an objective housed in a distal end of said inside tube, an optical system for transporting images, housed in said inside tube, an eye-piece arranged in said rotating tube and a view port closing a proximal opening of said handle;

wherein said handle comprises several independent control devices, each comprising a control ring surrounding said handle in a turning manner, a cylindrical mount housed in a sliding maimer in said rotating tube, and a coupling system coupling said control ring to said mount, so that rotation of said control ring controls longitudinal displacement of said mount inside said rotating tube, rotational movements of said rotating tube and said control ring and translation movements of said mount of each control device being independent from one another.

2. The deviated distal rotary viewing endoscope according to claim 1, wherein said mount of each control device comprises at least a first external radial pin housed in a sliding manner in a first longitudinal slot formed in said rotating tube, an end of said pin being housed in a running manner in an annular internal groove arranged in a sliding ring surrounding in a sliding manner said rotating tube and housed in a sliding manner in the handle, said sliding ring having a second external radial pin housed in a sliding manner in a second longitudinal slot arranged in the handle, an end of said second pin being housed in a sliding manner in an internal helicoidal groove arranged in the control ring.

3. The deviated distal rotary viewing endoscope according to claim 1, wherein one of said control devices is a focusing control device, the mount of said focusing control device housing fixedly said eye-piece.

4. The deviated distal rotary viewing endoscope according to claim 3, wherein the mount of said focusing control device has a distal opening acting as a field diaphragm and positioned in a distal focal plane of said eye-piece.

5. The deviated distal rotary viewing endoscope, according to claim 3, wherein one of said control devices is a reticle rotation control device, the focusing control device mount having a tubular cylindrical proximal part and a tubular cylindrical distal part with an outer diameter smaller than that of said proximal part, said reticle rotation control device further comprising:

a cylindrical tube supporting a reticle and surrounding in a turning manner said distal part of the focusing control device mount, said reticle support tube having an outside diameter substantially identical to that of said internal tube and a distal opening acting as a field diaphragm, said reticle support tube being coupled to said focusing control device mount so that said reticle is maintained in a distal focal plane of said eye-piece;

a control ring surrounding in a turning manner said handle;

a tubular cylindrical reticle rotation control device mount housed in a sliding manner in the rotating tube 18 and driven in translation by a rotation movement of the control ring of said reticle rotation control device;

a cylindrical coupling tube coupling the mount of said reticle rotation control device to said reticle supporting tube and having a proximal part surrounding said reticle supporting tube and a distal part surrounding a proximal end of the inside tube, and being surrounded by the reticle rotation control device mount;

a first coupling system rotatably coupling said coupling tube to said reticle supporting tube, so that a rotation of said coupling tube causes said reticle supporting tube to turn; and a second coupling system coupling said coupling tube to the reticle rotation control device mount, so that a translational movement of said reticle rotation control device mount causes said coupling tube to turn.

6. The deviated distal rotary viewing endoscope, according to claim 5, wherein said tubular distal part of said focusing control device mount has an outside annular groove housing in a running manner an end of an internal radial pin formed in a proximal part of said reticle supporting tube, said coupling tube having a proximal part comprising a longitudinal slot housing in a running manner an external radial pin formed on a distal part of said reticle supporting tube, a distal part of the coupling tube having a helicoidal slot housing an external radial pin formed on the reticle rotation control device mount.

7. The deviated distal rotary viewing endoscope according to claim 1, wherein one of said control devices is a viewing angle variation control device, the mount of said viewing angle variation control device surrounding in a sliding manner said proximal extension of said inside tube and being integral with a cylindrical maneuvering tube surrounding in a sliding manner said internal tube, a longitudinal displacement of said maneuvering tube causing the deviator prism to tilt around a transversal axis perpendicular to a viewing axis of the endoscope.

8. The deviated distal rotary viewing endoscope according to claim 7, wherein:

a distal end of said endoscopic probe comprises an end cap having a transverse distal side affixed to said distal end of said external tube, and a longitudinal flat side affixed to a longitudinal notch arranged in a distal part of said external tube;

said distal end cap comprises an internal protuberance having a square shape and a longitudinal part affixed to a distal end of a support piece having two proximal longitudinal lugs facing each other;

said deviator prism is housed affixed in a prism support fixed in a pivoting manner between said two lugs, said prism support being coupled to a distal end of said maneuvering tube, so that a longitudinal displacement of said maneuvering tube causes said prism support to tilt around said transversal axis.

9. The deviated distal rotary viewing endoscope according to claim 1, wherein:

said deviator prism is a partial reflection prism characterized by a unidirectional inversion of an image transmitted by said deviator prism; and a partial reflection correcting prism characterized by a unidirectional inversion of an image transmitted by the correcting prism is housed affixed in a proximal end of said turning tube and radially positioned so that an image transmitted by said endoscope has no inversion relative to reality.

10. The deviated distal rotary viewing endoscope according to claim 1, wherein:

said distal deviator prism is a partial reflection prism characterized by a unidirectional inversion of an image transmitted by said deviator prism; and a partial reflection correcting prism characterized by a unidirectional inversion of an image transmitted by said correcting prism is housed affixed between two lenses in the inside tube of the endoscopic probe and radially positioned in such a manner that the image transmitted by said endoscope has no inversion relative to reality.

11. The deviated distal rotary viewing endoscope according to claim 1, wherein:

said distal deviator prism is a total reflection prism characterized by a bidirectional inversion of the image transmitted by the prism; and a series of lenses comprising said optical system is calculated so that an image transmitted by said endoscope has no inversion relative to reality.

12. The deviated distal rotary viewing endoscope according to claim 1, further comprising a stopper device designed to limit the range of rotation of said endoscopic probe.

13. The deviated distal rotary viewing endoscope according to claim 12, wherein said stopper device comprises a longitudinal pin integral with a proximal side of said probe rotation control ring, said pin coming out inside said handle so as to come into contact with an internal radial pin integral with the handle.

14. The deviated distal rotary viewing endoscope according to claim 12, further comprising a lighting device comprised of a bundle of optical fibers housed in an annular volume between said internal and external tubes;

wherein a distal end of said bundle opens into at least one lighting windows arranged in a distal part of said external tube of the endoscopic probe so as to produce a lighting field covering an optical field of said endoscopic probe, a proximal end of said bundle of fibers opening inside said handle through a hole made in a distal part of said rotating tube, said proximal end of said bundle of fibers being housed in a lateral seat integral with said handle.

15. The deviated distal rotary viewing endoscope according to claim 14, wherein a proximal part of the bundle of fibers is coiled around the rotating tube in order to prevent a rotation of said endoscopic probe from causing stresses that are able to break the fibers of said bundle.

* * * * *